United States Patent
Qiu (10) Patent No.: US 10,932,498 B2
(45) Date of Patent: Mar. 2, 2021

(54) ATOMIZER AND ELECTRONIC CIGARETTE HAVING THE SAME

(71) Applicant: JOYETECH EUROPE HOLDING GMBH, Zug (CH)

(72) Inventor: Wei-Hua Qiu, ChangZhou (CN)

(73) Assignee: JOYETECH EUROPE HOLDING GMBH, Zug (CH)

( * ) Notice: Subject to any disclaimer, the term of this patent is extended or adjusted under 35 U.S.C. 154(b) by 385 days.

(21) Appl. No.: 15/987,907

(22) Filed: May 24, 2018

(65) Prior Publication Data

US 2018/0263294 A1 Sep. 20, 2018

Related U.S. Application Data (63) Continuation-in-part of application No. PCT/CN2016/105165, filed on Nov. 9, 2016.

(30) Foreign Application Priority Data

Nov. 25, 2015 (CN) .......................... 201510831537.7

(51) Int. Cl.
  *A24F 47/00* (2020.01)
  *A61M 15/00* (2006.01)

(52) U.S. Cl.
  CPC ............ *A24F 47/008* (2013.01); *A24F 47/00* (2013.01); *A61M 15/0021* (2014.02)

(58) Field of Classification Search
  CPC ......... A24F 40/40; A24F 47/008; A24F 40/10
  See application file for complete search history.

(56) References Cited

U.S. PATENT DOCUMENTS

| | | | |
|---|---|---|---|
| 2013/0228191 A1 | 9/2013 | Newton | |
| 2014/0130816 A1* | 5/2014 | Liu | A24F 47/008 |
| | | | 131/329 |
| 2015/0034105 A1 | 2/2015 | Liu | |
| 2015/0189919 A1* | 7/2015 | Liu | A24F 47/008 |
| | | | 131/329 |
| 2015/0245669 A1 | 9/2015 | Cadieux et al. | |
| 2016/0192707 A1* | 7/2016 | Li | H05B 3/00 |
| | | | 131/329 |
| 2017/0006923 A1* | 1/2017 | Li | B67D 99/00 |
| 2017/0273359 A1* | 9/2017 | Liu | A24F 47/008 |

FOREIGN PATENT DOCUMENTS

| | | |
|---|---|---|
| CN | 103462224 A | 12/2013 |
| CN | 104207330 A | 12/2014 |
| CN | 204157650 U | 2/2015 |
| CN | 204169056 U | 2/2015 |
| CN | 204351070 U | 5/2015 |
| CN | 204393353 U | 6/2015 |

(Continued)

*Primary Examiner* — Eric Yaary
(74) *Attorney, Agent, or Firm* — ScienBiziP, P.C.

(57) ABSTRACT

An atomizing head and a ventilation assembly are included in an atomizer for an electronic cigarette. The atomizing head includes an atomizing core and an atomizing tube. The circumference of the atomizing core defines airflow channels, so that air can flow into the atomizing core. This avoids the leakage caused by negative pressure when a user is inhaling smoke. The atomizer causes outside air to be more fully mixed with the smoke generated from liquid tobacco, and the user's experience is improved.

15 Claims, 10 Drawing Sheets

(56) References Cited

FOREIGN PATENT DOCUMENTS

| | | |
|---|---|---|
| CN | 204444248 U | 7/2015 |
| CN | 104939326 A | 9/2015 |
| CN | 204599341 U | 9/2015 |
| CN | 204635088 U | 9/2015 |
| CN | 204742640 U | 11/2015 |
| CN | 204763435 U | 11/2015 |
| CN | 105286091 A | 2/2016 |
| CN | 205180374 U | 4/2016 |

* cited by examiner

FIG. 16 ary application will be given with reference to the accompanying drawings. A number of specific details are set forth in the following description so as to enable full understanding of the present application. However, the present application can be implemented in many ways different from those described herein, and those skilled in the art can make improvements without violating the contents of the present application. Therefore, the present application is not to be considered as limiting the scope of the embodiments described herein.

ATOMIZER AND ELECTRONIC CIGARETTE HAVING THE SAME

FIELD

The present disclosure relates to an electronic cigarette, and more particularly to an atomizer and an electronic cigarette having the atomizer.

BACKGROUND

An electronic cigarette can atomize liquid tobacco stored in a smoke cartridge into smoke, which can be inhaled like traditional cigarettes. Usually, the electronic cigarette includes an atomizer and a battery device. The atomizer includes a heating coil. The liquid tobacco stored in the atomizer can be atomized by the heating coil to generate smoke. In current atomizer, the liquid tobacco is stored in a container. The storage container could be a liquid cup in the atomizer or a divided space of an atomizing tube. A baffle piece is positioned on an upper cover of the storage container for sealing the storage container, and several holes are defined on the baffle piece. When the electronic cigarette is in work, the liquid tobacco can flow out from the holes. However, during transportation or storage, the electronic cigarettes can be shaken, which results in leakage of the liquid tobacco. The atomizer defines an air inlet at the bottom, and an end of the air inlet is in communication with a liquid guide, the other end of the air inlet is in communication with the outside. Since the holes are totally open all the time, and liquid tobacco cannot be prevented from leaking and being wasted when in use. In addition, when the user is inhaling, a negative pressure is produced, and the liquid tobacco of the liquid guide can easily leak from the air inlet. This reduces utilization rate of the liquid tobacco and user's experience.

BRIEF DESCRIPTION OF THE DRAWINGS

Many aspects of the disclosure can be better understood with reference to the following drawings. The components in the drawings are not necessarily drawn to scale, the emphasis instead being placed upon clearly illustrating the principles of the disclosure. Moreover, in the drawings, like reference numerals designate corresponding parts throughout the several views.

DETAILED DESCRIPTION

Detailed description of specific embodiments of the present application will be given with reference to the accompanying drawings. A number of specific details are set forth in the following description so as to enable full understanding of the present application. However, the present application can be implemented in many ways different from those described herein, and those skilled in the art can make improvements without violating the contents of the present application. Therefore, the present application is not to be considered as limiting the scope of the embodiments described herein.

Several definitions that apply throughout this disclosure will now be presented.

The term "coupled" is defined as coupled, whether directly or indirectly through intervening components, and is not necessarily limited to physical connections. The connection may be such that the objects are permanently coupled or releasably coupled. The term "substantially" is defined to be essentially conforming to the particular dimension, shape, or other feature that the term modifies, such that the component need not have that exact feature. The term "comprising," when utilized, means "including, but not necessarily limited to"; it specifically indicates open-ended inclusion or membership in the so-described combination, group, series, and the like.

When an element is considered to be "fixed to" another element, it can be either directly fixed on another element or indirectly fixed on another element with a centered element. When an element is considered to be "coupled with" another element, it can be either directly coupled with another element or indirectly coupled with another element.

Unless otherwise defined, all technical and scientific terms used herein have the same meaning as commonly understood by one skilled in the art. The terms used in specification of the present application are only for describing specific embodiments, and are not intended to limit the present application. The terms "and/or" used herein includes any and all combinations of one or more of associated listed items.

FIGS. 1 to 4 show an atomizer 100 of a first embodiment. The atomizer 100 includes a liquid storage assembly 1 and an atomizing assembly 2. The upper portion of the atomizing assembly 2 is coupled to the liquid storage assembly 1. The liquid storage assembly 1 is sleeved over the upper portion of the atomizing assembly 2. An inner cavity of the liquid storage assembly 1 forms a liquid storage cavity 3. The lower portion of the atomizing assembly 2 can be suspended in the liquid storage cavity 3, or can abut against an inner surface of the lower portion of the liquid storage assembly 1. The liquid storage cavity 3 is configured to store liquid tobacco, therefore the atomizing assembly 2 is effectively immersed in the liquid storing cavity 3. The liquid tobacco stored in the liquid storage cavity 3 is absorbed and atomized by the atomizing assembly 2 to generate smoke, and a user inhales the smoke through a cigarette holder 4. The liquid storage assembly 1 provides a liquid storage cavity 3 for storing liquid tobacco, and also forms an outline of the atomizer 100.

In order to solve the problem of leaking liquid tobacco, in the first embodiment of the atomizer 100, the inner cavity of the liquid storage assembly 1 forms the liquid storage cavity 3. The liquid storage cavity 3 is sealed because of the function of storing liquid tobacco. The atomizing assembly 2 is received in the liquid storage assembly 1, thus the liquid storage assembly 1 provides a closed space for the atomizing assembly 2. Liquid tobacco is stored in the liquid storage cavity 3, so that the atomizing assembly 2 is steeped in the liquid tobacco. In this way, the leakage situation can be avoided, and the utilization rate of the liquid tobacco can be improved.

Figure 3:
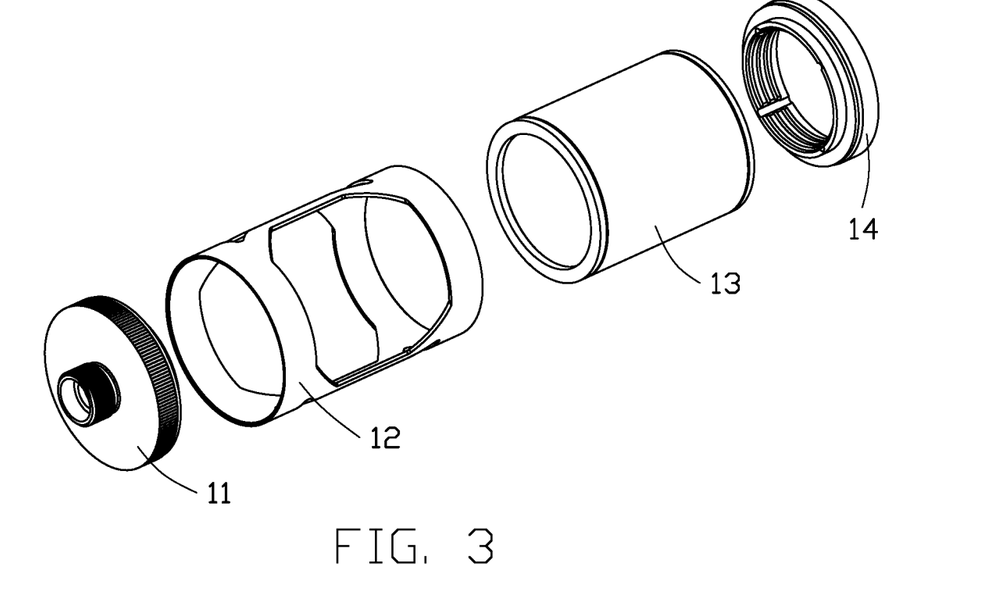
FIG. 3 is an exploded view of the liquid storage assembly of the atomizer shown in FIG. 1.
Figure 4:
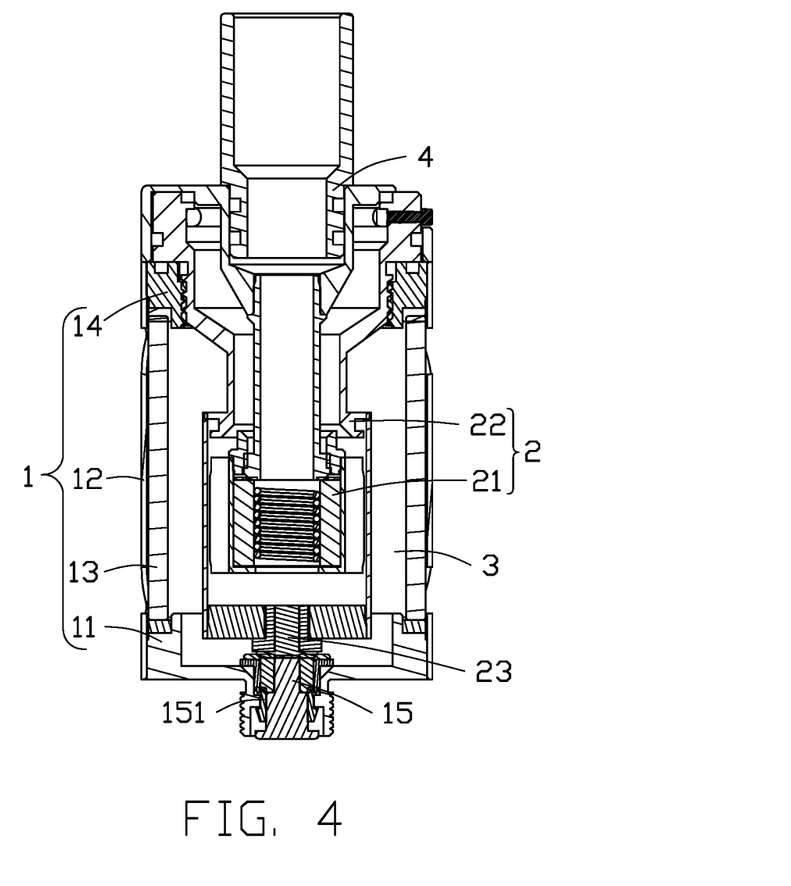
FIG. 4 is a cross-sectional view along the direction A-A of the atomizer shown in FIG. 1.

Referring to FIG. 3, in the first embodiment of the atomizer 100, the liquid storage assembly 1 includes a base 11, a supporting sheath 12, a glass outer tube 13, and a fixing member 14. The supporting sheath 12 sleeves on the glass outer tube 13. The base 11 is fixed at the lower end of the supporting sheath 12. Accordingly, the fixing member 14 is fixed at the upper end of the supporting sheath 12. When all parts of the liquid storage assembly 1 are assembled, the atomizing assembly 2 can be received in the liquid storage assembly 1. In the illustrated embodiment, the fixing member 14 is a lantern ring with internal threads, and external threads are defined on the atomizing assembly 2, so that the atomizing assembly 2 can be fixed and sealed on the liquid storage assembly 1.

A first electrode 15 is positioned on the liquid storage assembly 1, and a second electrode 23 is positioned on the atomizing assembly 2. The first electrode 15 is electrically connected with the second electrode 23. In the first embodiment, the first electrode 15 passes through a first through hole 112 defined on the base 11. In order not to damage the sealing of the liquid storage assembly 1, the first electrode 15 and the first through hole 112 can be assembled as an interference fit or threaded connection. When the first electrode 15 and the first through hole 112 are assembled together as an interference fit, a first sealing member 151 can be positioned between the first electrode 15 and the first through hole 112. The first sealing member 151 can be a gasket made of silicon or rubber.

Figure 5:
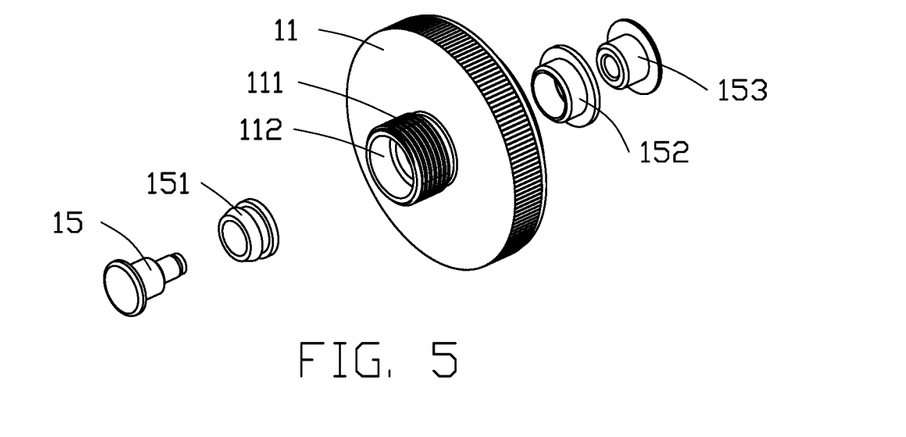
FIG. 5 is an exploded view of a first electrode and a base of the atomizing assembly of the atomizer shown in FIG. 1.

Referring to FIG. 5, when the first electrode 15 passes through the first through hole 112, a first electrode connecting tube 153 matched to the first electrode 15 is positioned at another side of the base 11. The first electrode connecting tube 153 is clipped in the first through hole 112 through a first silicon gasket 152. The existence of the first electrode connecting tube 153 and the first silicon gasket 152 improves the sealing between the first electrode 15 and the first through hole 112. When the first electrode 15, the first electrode connecting tube 153, and the first silicon gasket 152 are assembled, the first electrode 15 can be inserted into the first electrode connecting tube 153, and both of them can continue conducting. In order to firmly connect the atomizer 100 to a battery of an electronic cigarette, in the illustrated embodiment, a connection portion 111 is positioned on the base 11. The connection portion 111 can be threaded or with a buckle, thus the atomizer 100 has a reliable connection with the battery of the electronic cigarette.

Figure 1:
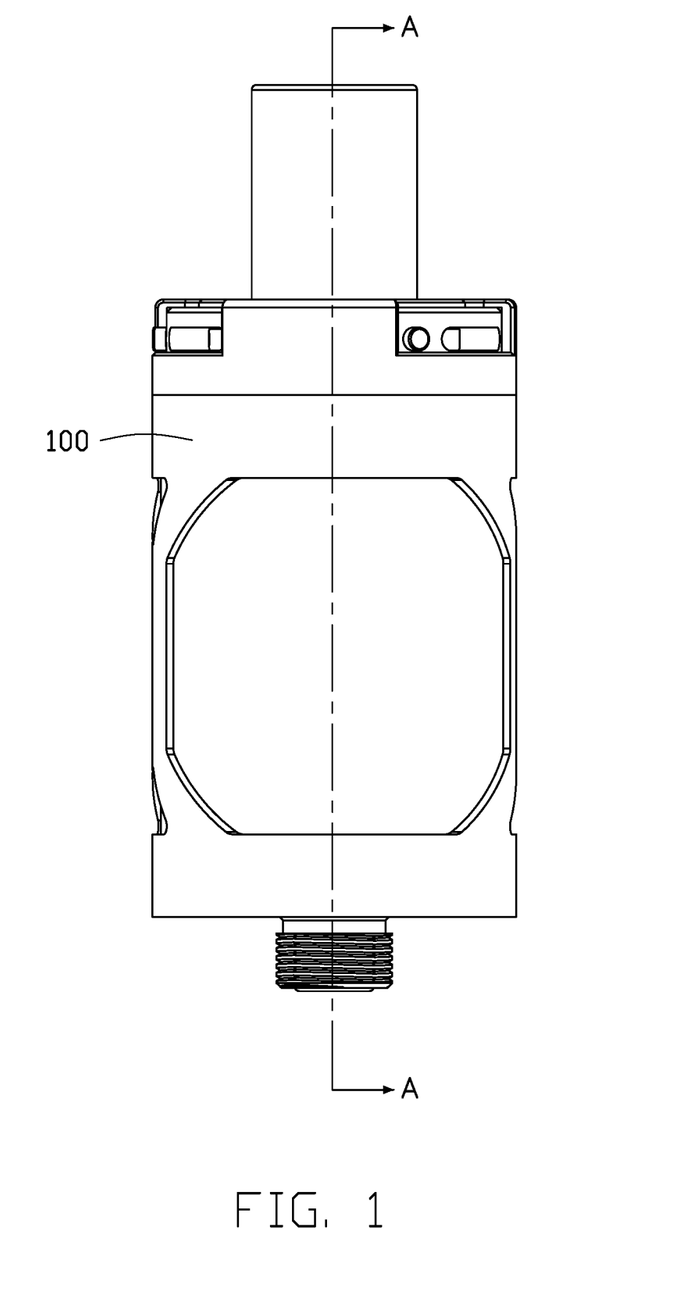
FIG. 1 is a front view of a first embodiment of an atomizer.
Figure 2:
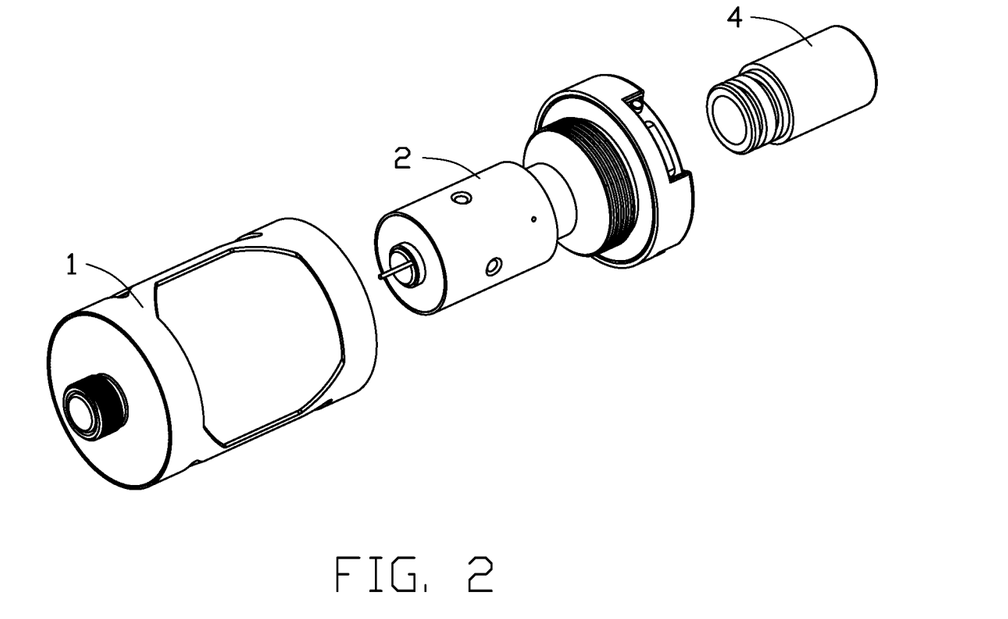
FIG. 2 is an exploded view of a liquid storage assembly and an atomizing assembly of the atomizer (including a cigarette holder) shown in FIG. 1.
Figure 6:
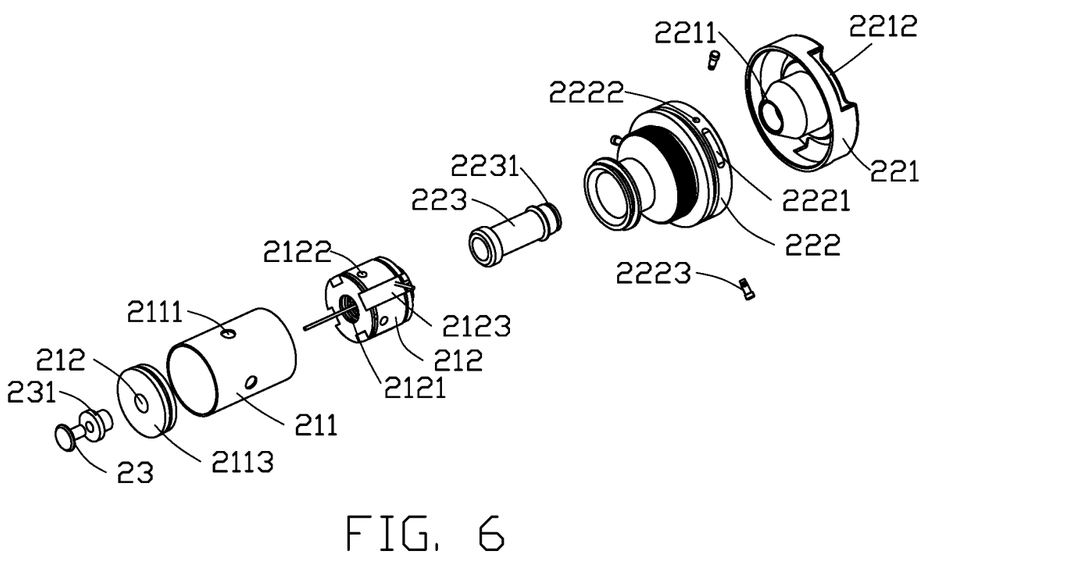
FIG. 6 is an exploded view of the atomizing assembly of the atomizer shown in FIG. 1.

Referring to FIG. 2 and FIG. 6, in the first embodiment, the atomizing assembly 2 includes an atomizing head 21 and a ventilation assembly 22. The atomizing head 21 is fixedly connected to the ventilation assembly 22. The second electrode 23 is positioned on the atomizing head 21. Specifically, the atomizing head 21 includes an atomizing core 212 and an atomizing tube 211. The atomizing tube 211 is sleeved over the atomizing core 212. The second electrode 23 is positioned at the bottom of the atomizing tube 211. The upper end of the atomizing tube 211 is fixed to the ventilation assembly 22.

Furthermore, in the first embodiment, preferably, the atomizing tube 211 further includes an atomizing head base 2113 positioned at the lower end of the atomizing tube 211. A second through hole 2112 is defined on the atomizing head base 2113. The second electrode 23 passes through the second through hole 2112 and is fixed to the atomizing head base 2113. A second sealing member 231 is positioned between the second electrode 23 and the second through hole 2112, thus the reliability of sealing is improved, and too much liquid tobacco is prevented from entering the atomizing head 21, thus user will not inhale liquid tobacco.

Figure 7:
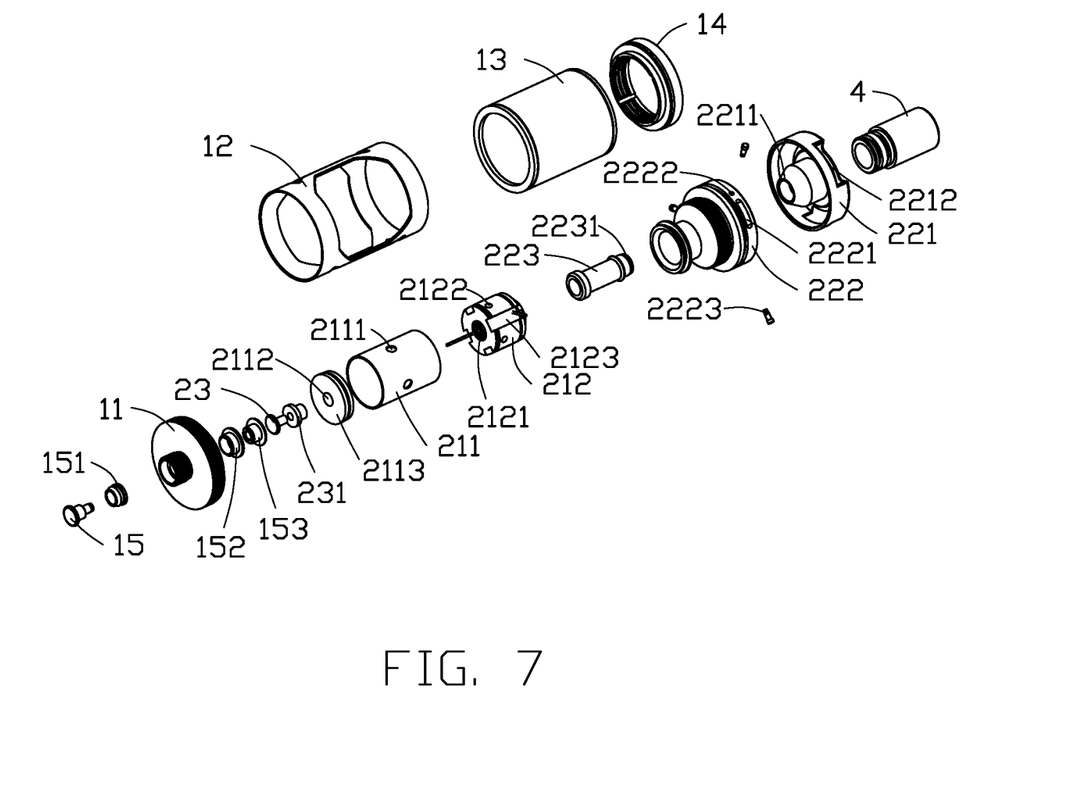
FIG. 7 is an exploded view of the atomizer of the first embodiment.

FIG. 7 shows the atomizer 100 of the first embodiment. The atomizing assembly 2 includes an air adjusting device. The air adjusting device is positioned on the ventilation assembly 22. The air adjusting device can adjust the amount of airflow in the atomizer 100, to adapt to different users' requirements. Specifically, the ventilation assembly 22 includes an inner tube 223, an outer tube 222 and a ventilation cover 221. An end of the outer tube 222 is fixed to the atomizing head base 2113, another end of the outer tube 222 is fixed to the ventilation cover 221. The outer tube 222 is sleeved over the inner tube 223. In the first embodiment, preferably, an inner tube upper flange 2231 is positioned at the outside of an end of the inner tube 223. A ventilation cover lower flange 2211 is positioned at the lower end of the ventilation cover 21. During assembly, the end of the inner tube 223 with the inner tube upper flange 2231 is pressed into the outer tube 222, the inner tube upper flange 2231 abuts against the ventilation cover lower flange 2211 as an interference fit, so that the inner tube 223 is fixed in the outer tube 222. The other end of the inner tube 223 is suspended. Therefore, the present disclosure is different from the current technology, that air is injected from the bottom of the atomizing core, and the air inlet of the atomizing core is exposed to the outside of the atomizer. In the first embodiment, the atomizing tube 211 is sleeved over the atomizing core 212. The atomizing tube 211, as a part of the atomizing assembly 2, is positioned in the liquid storage cavity 3, thus leaking should not occur. Even if the liquid tobacco is leaking, the leaked liquid tobacco is still in the atomizer 100, the liquid tobacco will not leak out from the atomizer 100. In the first embodiment, the air flow and the liquid tobacco flow are separated. Air can enter the atomizing core 212 from upper portion, middle portion, or lower portion of the atomizer 100 through an airflow channel 2123, and the air mixes with the smoke in the atomizing core 212, and it is then that the user inhales the air/smoke mixture.

Specifically, the air adjusting device is formed by the outer tube 222 and the ventilation cover 221. The ventilation cover 221 is rotatably sleeved over the outer tube 222. A first ventilation portion 2221 is defined on the outer tube 222. A second ventilation portion 2212 is defined on the ventilation cover 221. Since the ventilation cover 221 is rotatably sleeved over the outer tube 222, the port size between the first ventilation portion 2221 and the second ventilation portion 2212 is adjustable by screwing the ventilation cover 221. Preferably, in order to limit a rotation angle of the ventilation cover 221, and to remind user that the port size between the first ventilation portion 2221 and the second ventilation portion 2212 is reaching the maximum or the minimum size. In the illustrated embodiment, pin bolts 2223 are positioned on the outer tube 222. The pin bolts 2223 are inserted into the installation holes 2222 defined on the outer tube 222, and the pin bolts 2223 are an interference fit with the installation holes 2222. Therefore, in screwing the ventilation cover 221, the pin bolts 2223 limit the rotation angle of the ventilation cover 221.

Figure 8:
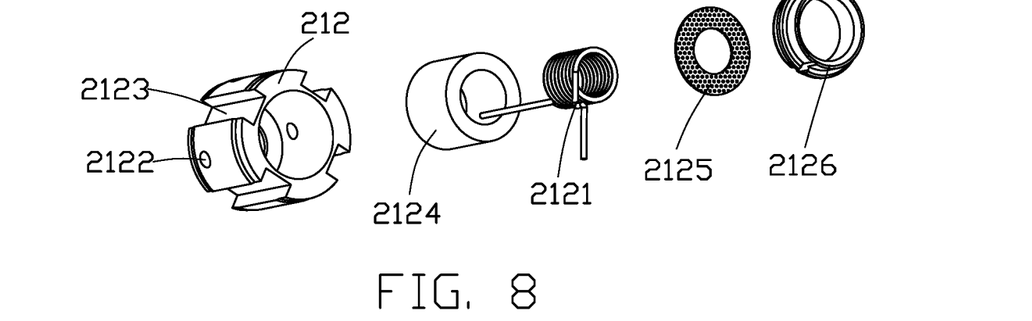
FIG. 8 is an exploded view of an atomizing core of the atomizer shown in FIG. 7.

Referring to FIG. 8, the atomizing core 212 includes at least one airflow channel 2123 defined at an outer side of the circumference of the atomizing core 212. In the illustrated embodiment, there are four airflow channels 2123. When the external air enters the atomizer 100, the air can flow into an interior of the atomizing core 212 through the airflow channels 2123. The atomizing core further includes a spiral-shaped heating coil 2121 and a liquid absorbing element 2124. The heating coil 2121 is positioned vertically, and a center channel of the heating coil 2121 can be a part of a smoke channel. The smoke generated from liquid tobacco is inhaled by the user through the smoke channel. Preferably, the airflow channels 2123 are each a groove defined on a surface of the atomizing core 212, and the direction of the each groove is parallel with an axial direction of the atomizing core 212. The periphery of the atomizing core 212 is divided into several liquid inlet areas by several airflow channels 2123. Each liquid inlet area corresponds to an assisting liquid inlet 2122. The assisting liquid inlets 2122 communicate with liquid inlets 2111 defined on the atomizing tube 211, so that liquid tobacco can be absorbed by the liquid absorbing element 2124 through the liquid inlet 2111 and the assisting liquid inlet 2122. When the heating coil 2121 is energized, the liquid tobacco can be continuously heated and atomized. The liquid absorbing element 2124 can be at least one or a combination of cotton material, porous ceramic, porous graphite, and foam metal. The heating coil 2121 is wrapped in the liquid absorbing element 2124, and both are arranged in the atomizing core 212. To prevent liquid tobacco from fizzing and sputtering when liquid tobacco is heated, a filter screen 2125 is positioned on the upper end of the liquid absorbing element 2124. The filter screen 2125 can be made of steel. Furthermore, an atomizing core cover 2126 is positioned on the upper end of the atomizing core 212 to press together the filter screen 2125, the liquid absorbing element 2124, and the heating coil 2121. The filter screen 2125, the liquid absorbing element 2124, and the heating coil 2121 are tightly arranged in the atomizing core 212. In order to keep the airflow smooth, the atomizing core cover 2126 can be unsealed and can define a through hole at the top thereof.

Figure 9:
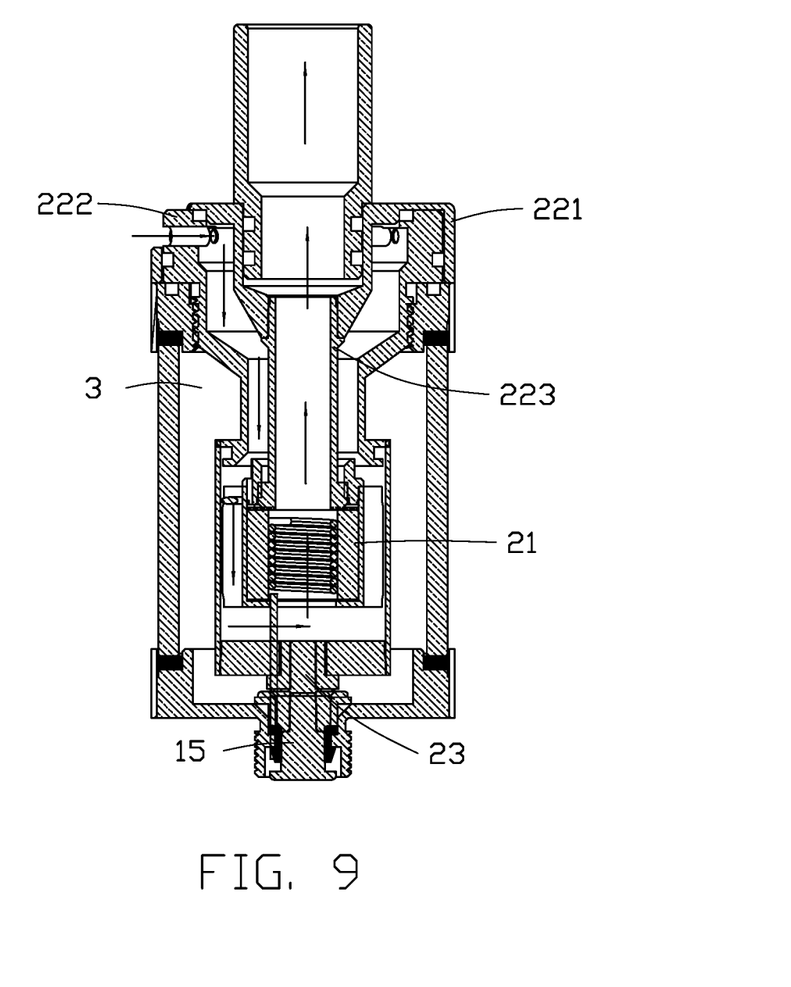
FIG. 9 is a schematic view of an air flow direction in the atomizer of the first embodiment.
Figure 10:
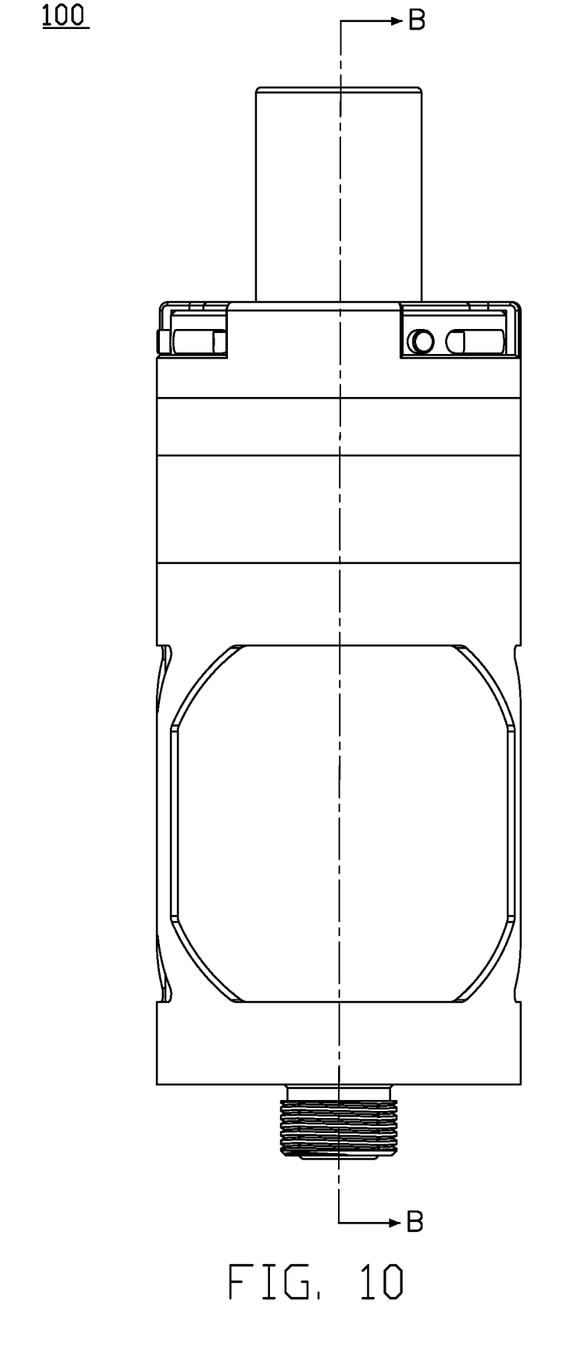
FIG. 10 is a front view of a second embodiment of an atomizer.
Figure 11:
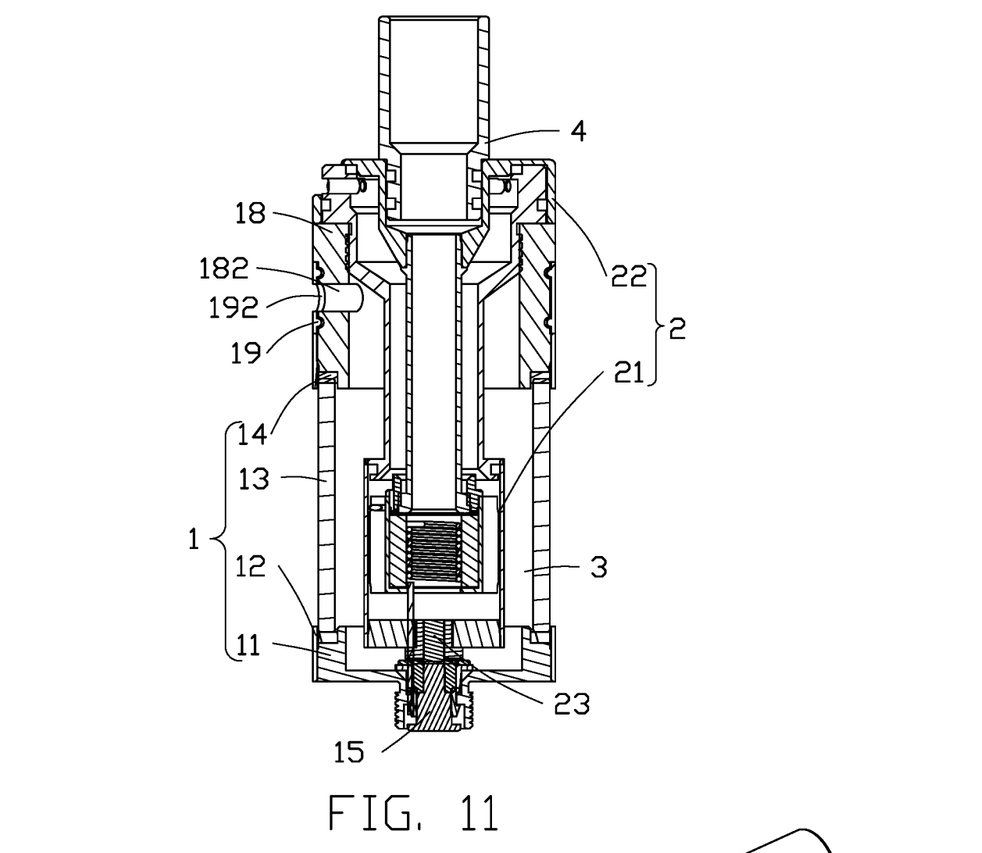
FIG. 11 is a cross-sectional view along the direction B-B of the atomizer shown in FIG. 10.
Figure 12:
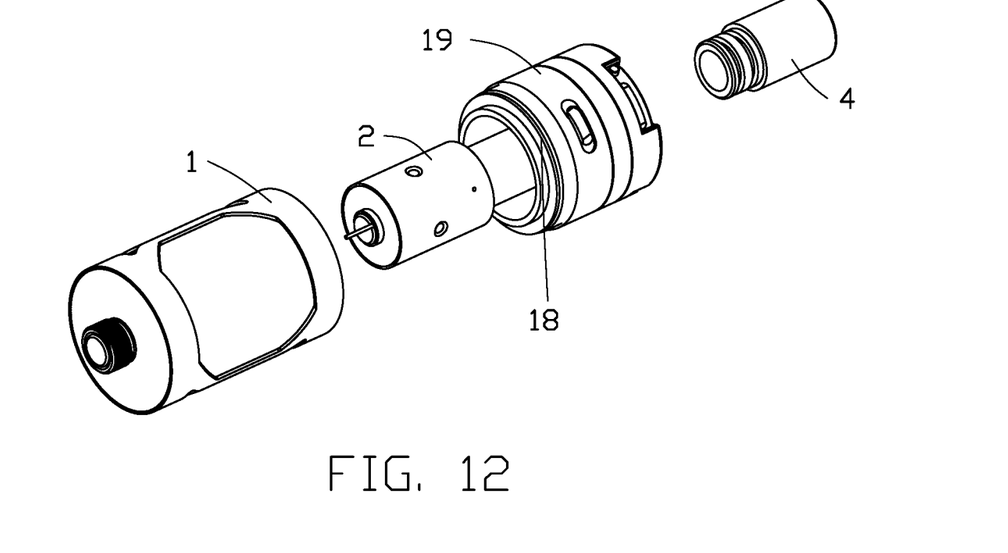
FIG. 12 is an exploded view of a liquid storage assembly and an atomizing assembly of the atomizer (including a cigarette holder) shown in FIG. 10.
Figure 13:
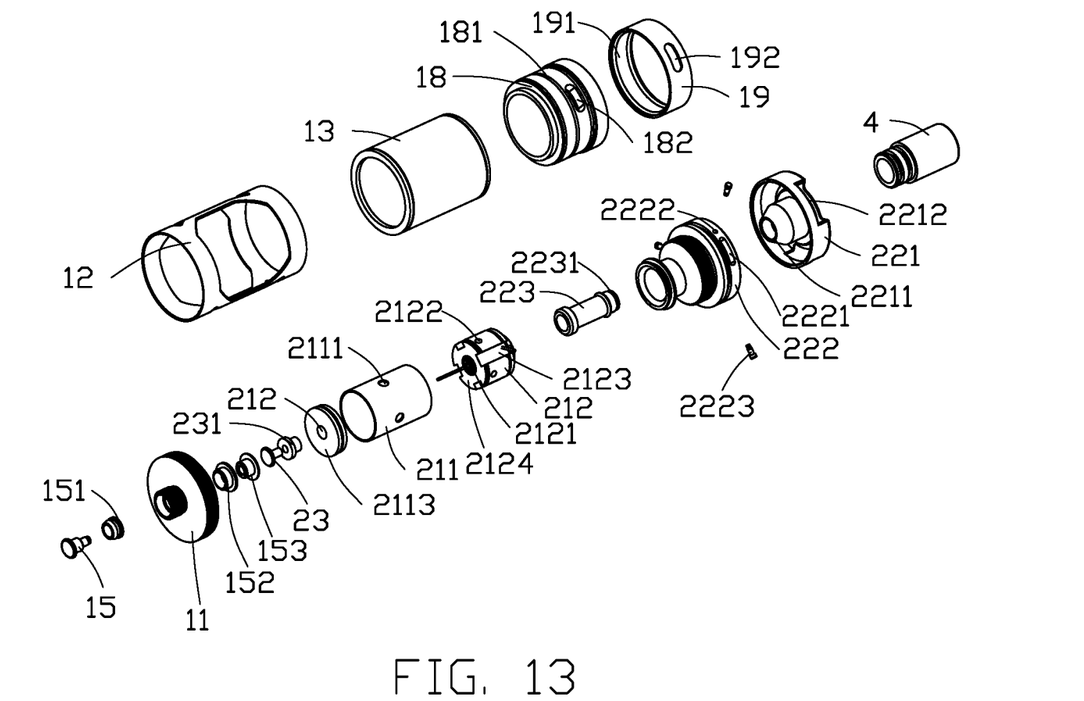
FIG. 13 is an exploded view of the atomizer shown in FIG. 10.

Referring to FIG. 9, the direction of arrows shows the direction of airflow. When the ventilation cover 221 is rotated, causing the first ventilation portion 2221 to communicate with the second ventilation portion 2212, external air enters the atomizer 100 through the second ventilation portion 2212 and the first ventilation portion 2221. Then, the air enters the atomizing head 21 through the channel between the outer tube 222 and the inner tube 223. Liquid tobacco is heated to generate smoke in the atomizing head 21, and the air/smoke mixture is inhaled by user through the inner channel of the inner tube 223. When the liquid tobacco needs replenishment, the ventilation cover 221 can be rotated in reverse. With the help of the pin bolt 2223, the outer tube 222 is rotated accordingly and separated from the liquid storage assembly 1. Thereby, the user can inject new liquid tobacco into the liquid storage cavity 3. When the user finishes injecting liquid tobacco, the atomizing assembly 2 can be screwed back into the liquid storage assembly 1. The whole process of injecting liquid tobacco is convenient, and the atomizer 100 needs not be turned over.

Referring to FIG. 2 and FIGS. 4-6, an end of the heating coil 2121 is sandwiched between the second electrode 23 and the second sealing member 231. Another end of the heating coil 2121 is sandwiched between the atomizing head base 2113 and the second sealing member 231. The atomizing head base 2113, the atomizing tube 211, the ventilation cover 221, the fixing member 14, the supporting sheath 12, and the base 11 are made of electrically conductive materials. The first sealing member 151, the first silicon gasket 152, and the second sealing member 231 not only have a sealing function, but also have an insulating function. Therefore, the first electrode 15, the first electrode connecting tube 153 are insulated from the base 11. The second electrode 23 is insulated from the atomizing head base 2113. When the atomizing assembly 2 is assembled in the liquid storage assembly 1, and the liquid storage assembly 1 is connected with the battery, an end of the heating coil 2121 is electrically connected with a pole of the battery through the second electrode 23 and the first electrode 15, another end of the heating coil 2121 is electrically connected with another pole of the battery through the atomizing head base 2113, the atomizing tube 211, the ventilation cover 221, the fixing member 14, the supporting sheath 12, and the base 11.

FIGS. 10-13 show a second embodiment of an atomizer. The difference between the first embodiment and the second embodiment is that the atomizer of the second embodiment further includes a liquid inlet tube 18 and a liquid inlet adjusting ring 19.

In the second embodiment, the liquid inlet tube 18 is positioned on the atomizing assembly 2. Preferably, the liquid inlet tube 18 is sleeved over the outer tube 222. A liquid inlet tube flange 181 is positioned at a peripheral region of the liquid inlet tube 18, and a first liquid injection hole 182 is defined on the peripheral region of the liquid inlet tube 18. A liquid inlet adjusting ring flange 191 is positioned at an inner wall of the liquid inlet adjusting ring 19. A second liquid injection hole 192 is defined on a sidewall of the liquid inlet adjusting ring 19. The liquid inlet adjusting ring 19 is rotatably sleeved over the periphery of the liquid inlet tube 18 and will not slide down because of abutting against the liquid inlet adjusting ring flange 191 and the liquid inlet tube flange 181. The liquid inlet adjusting ring 19 can be made of solid metal, or ceramic material, or silicon, or rubber. The area between the first liquid injection hole 182 and the second liquid injection hole 192 is adjustable by rotating the liquid inlet adjusting ring 19, so that the first liquid injection hole 182 and the second liquid injection hole 192 can communicate or not.

The way of injecting liquid tobacco in the first embodiment is to separate the atomizing assembly 2 from the liquid storage assembly 1, then inject the liquid tobacco. In the second embodiment, the way of injecting liquid tobacco is to rotate the liquid inlet adjusting ring 19 to open the first liquid injection hole 182 and the second liquid injection hole 192. Liquid tobacco is then injected at a side of the atomizer 100. After injection, the liquid inlet adjusting ring 19 is rotated to stagger the first liquid injection hole 182 and the second liquid injection hole 192. In this way, the liquid storage assembly 1 is not separated from the atomizing assembly 2 in the whole process of injecting new liquid tobacco, and the operations of injecting new liquid tobacco are simplified.

Figure 14:
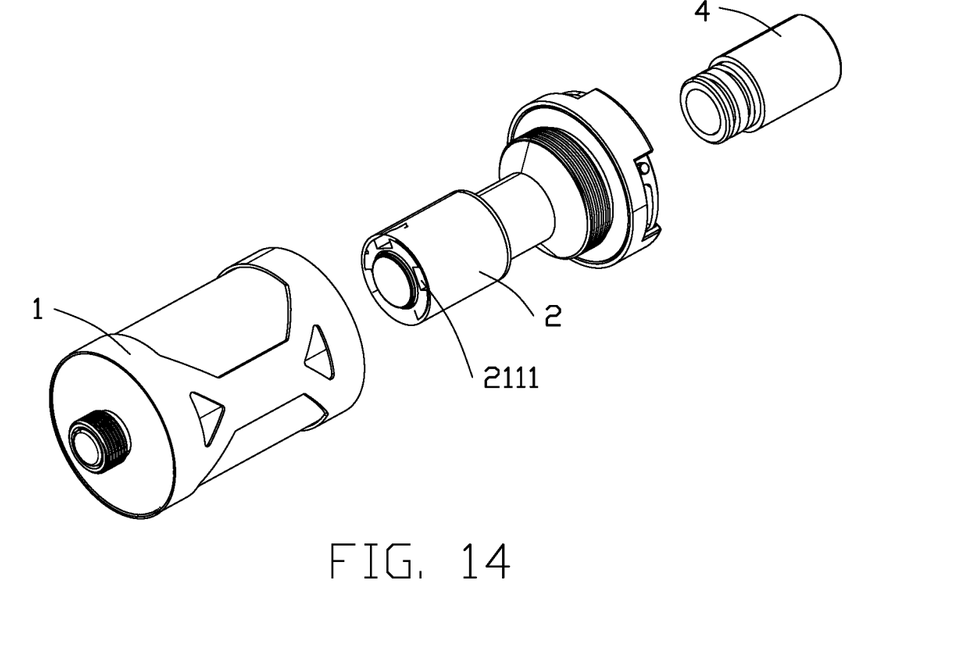
FIG. 14 is an exploded view of a liquid storage assembly and an atomizing assembly of the atomizer (including a cigarette holder) of a third embodiment.
Figure 15:
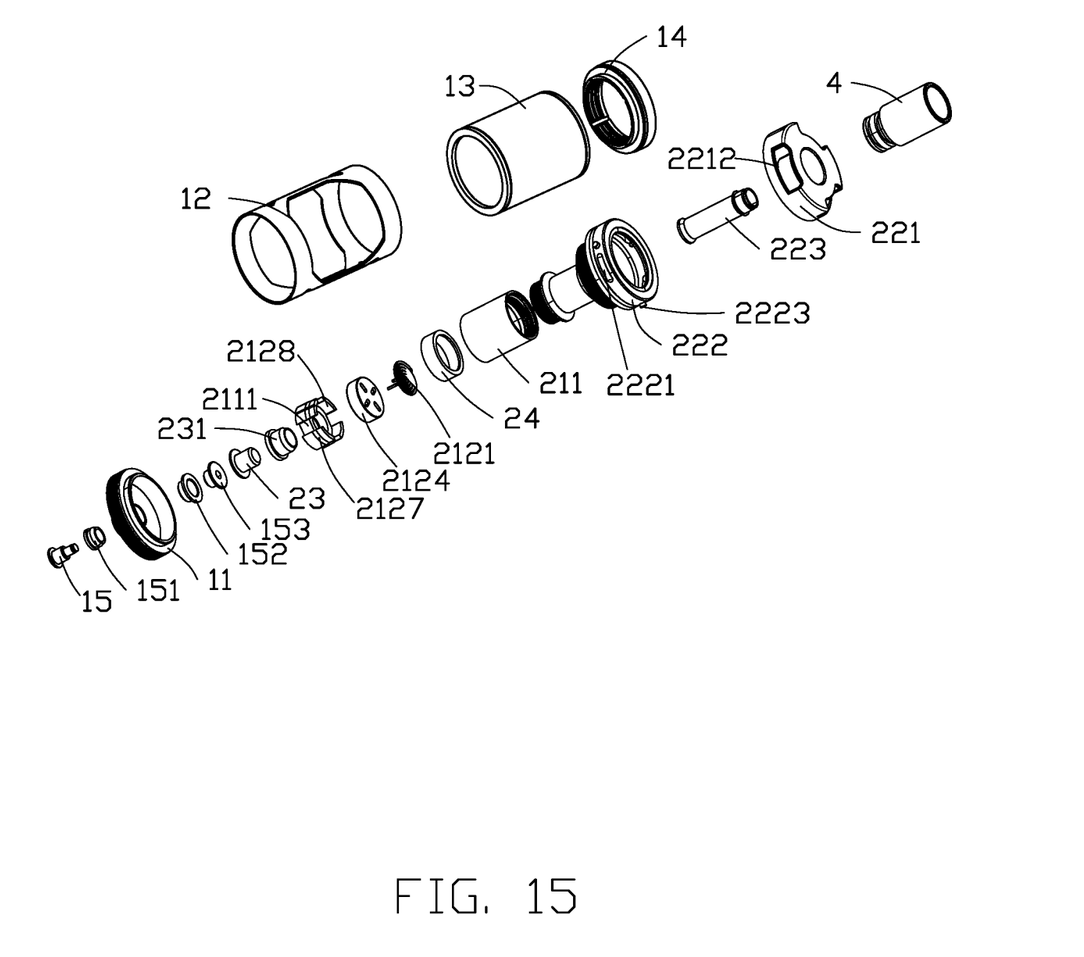
FIG. 15 is an exploded view of the atomizer of the third embodiment.

FIG. 14 and FIG. 15 show a third embodiment of an atomizer. The difference between the first embodiment and the third embodiment is that the heating coil 2121 of the third embodiment is positioned horizontally, and the liquid tobacco enters the atomizing assembly 2 from the bottom of the atomizing assembly 2. By contrast, the heating coil 2121 of the first embodiment is positioned vertically, and the liquid tobacco enters the atomizing assembly 2 from the sidewall of the atomizing assembly 2.

Specifically, in the third embodiment, the atomizer 100 includes a plate-shaped heating coil 2121. The atomizing core 212 includes an atomizing core base 2127 and a liquid absorbing element 2124. A concave portion 2128 is defined on the atomizing core base 2127. The heating coil 2121 and the liquid absorbing element 2124 are received in the concave portion 2128. The atomizing core base 2127 is fixed at the bottom of the atomizing tube 211. The second electrode 23 is sleeved at the bottom of the atomizing core base 2127. Several grooves are defined on the periphery of the atomizing core base 2127. When all parts of the atomizing core 212 are assembled, and the atomizing core 212 is combined with the ventilation assembly 22 to form the atomizing assembly 2, the grooves defined on the periphery of the atomizing core base 2127 become channels for liquid tobacco to enter the liquid absorbing element 2121. From the bottom of the atomizing core base 2127, the space between the grooves and the inner wall of the atomizing tube 221 forms a liquid inlet 2111. In the third embodiment, the liquid tobacco enters the atomizing assembly 2 from the bottom of the atomizing core 212. Compared with the first embodiment (sideways entry of the liquid tobacco), the liquid tobacco is more fully utilized in the third embodiment. This avoids liquid tobacco which is stored at the bottom of the liquid storage cavity 3 being wasted by not being absorbed by the atomizing assembly 2.

In the third embodiment, the atomizing assembly 2 includes a ventilation base 24. The ventilation base 24 is substantially annular. The ventilation base 24 is sleeved over the plate-shaped heating coil 2121. The inner ring of the ventilation base 24 is aligned with the inner tube 223, and abuts against the lower end of the inner tube 223. Several grooves or openings (not shown in FIGS) are defined on the upper edge of the ventilation base 24, to connect the upper edge of the ventilation base 24 and the lower edge of the ventilation base 24. Air can pass through the grooves or openings. The specific shape of the grooves or openings is not limited. The top surface of the liquid absorbing element 2124 defines holes communicating with grooves or openings defined at the lower edge of the ventilation base 24, so that airflow can pass through the holes to enter the liquid absorbing assembly 2124, and flow out from the center of the liquid absorbing assembly 2124. The plate-shaped hating coil 2121 is positioned on the top center portion of the liquid absorbing element 2124. When the absorbed liquid tobacco is heated to generate smoke, the smoke is accumulated in the inner ring of the ventilation base 24. External air passes through the second ventilation portion 2212 and the first ventilation portion 2221, and enters the space between the outer tube 222 and the inner tube 223, then flows down into the ventilation base 24. Since the upper end and the lower end of the ventilation base 24 are communicated, air flow can enter the liquid absorbing element 2124 and flow out from the top center of the liquid absorbing element 2124. At the same time, external air mixes with the smoke. The air/smoke mixture flows out from the inner space of the inner tube 223 for inhalation.

Figure 16:
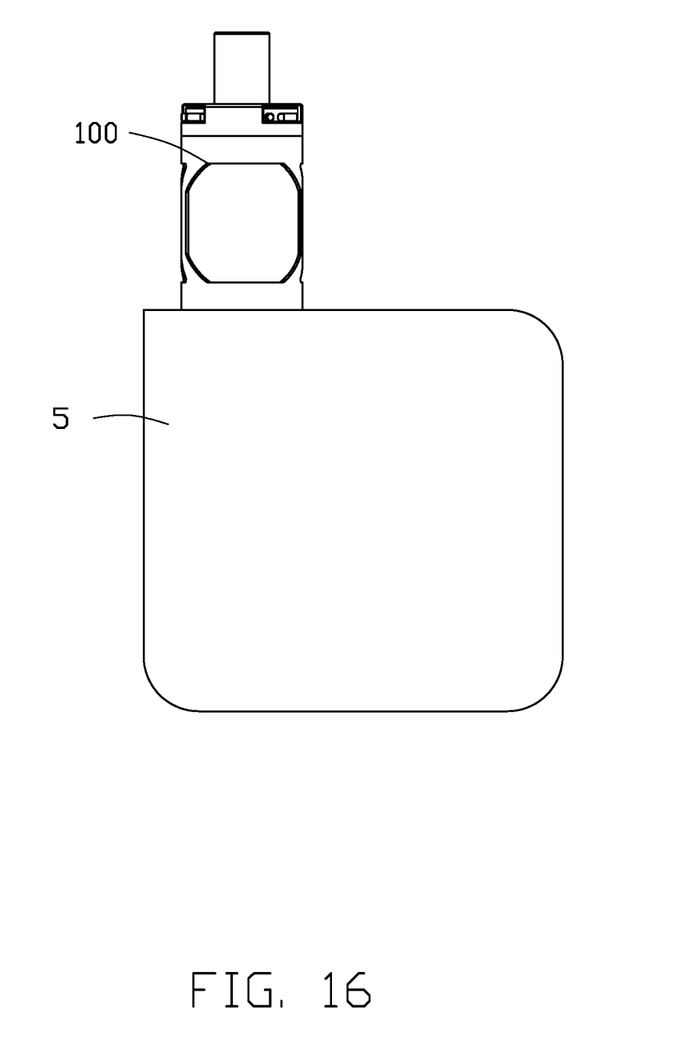
FIG. 16 is a front view of an electronic cigarette.

FIG. 16 shows an embodiment of an electronic cigarette. The electronic cigarette includes a battery 5 and any one of the atomizers 100 described in previous embodiments. The atomizer 100 is positioned on the upper portion of the battery 5, so that the user can hold the battery 5. The electronic cigarette has advantages provided by the atomizer 100. The present disclosure provides a reliable leak-proof electronic cigarette.

The embodiments shown and described above are only examples. Many details are often found in the art such as the other features of atomizers. Therefore, many such details are neither shown nor described. Even though numerous characteristics and advantages of the embodiments have been set forth in the foregoing description, together with details of the structure and function of the embodiments, the present disclosure is illustrative only, and arrangement of parts within the principles of the embodiments to the full extent indicated by the broad general meaning of the terms in which the appended claims are expressed.

What is claimed is:

1. An atomizer, comprising an atomizing assembly, the atomizing assembly comprising:
   an atomizing head comprising an atomizing core and an atomizing tube, the atomizing tube sleeved over the atomizing core, the atomizing tube comprises an atomizing head base positioned at a lower end of the atomizing tube, an outer side of circumference of the atomizing core defining a least one airflow channel; and
   a ventilation assembly fixed to an upper end of the atomizing tube, the at least one airflow channel communicating with the ventilation assembly, wherein the ventilation assembly comprises an inner tube, an outer tube and a ventilation cover, an end of the outer tube is fixed to the atomizing head base, another end of the outer tube is fixed to the ventilation cover, the outer tube is sleeved over the inner tube, an end of the inner tube is fixed to the ventilation cover, another end of the inner tube is suspended in the outer tube;
   wherein, air is capable of entering the atomizing core through the ventilation assembly and the airflow channel;
   the atomizer further comprises a liquid storage assembly, the liquid storage assembly defines a liquid storage cavity, an upper end of the atomizing assembly is sleeved over the liquid storage assembly, a lower end of the atomizing assembly is suspended in the liquid storage cavity, or abuts against a lower end surface of the liquid storage assembly;
   the liquid storage assembly comprises a first electrode, the atomizing assembly comprises a second electrode, the first electrode is electrically connected to the second electrode;
   the atomizing assembly further comprises an air adjusting device, the air adjusting device is positioned at an end of the ventilation assembly opposite to the atomizing head, the air adjusting device is configured to adjust the amount of airflow entering into the atomizer.

2. The atomizer as claimed in claim 1, wherein:
   the atomizing head is located at the lower end of the atomizing assembly,
   the ventilation assembly is located at the upper end of the atomizing assembly.

3. The atomizer as claimed in claim 1, wherein:
   the liquid storage assembly comprises a base, a supporting sheath, a glass outer tube, and a fixing member,
   the glass outer tube is received in the supporting sheath,
   the base is fixed at an end of the supporting sheath,
   the fixing member is fixed at another end of the supporting sheath, the atomizing assembly is fixed in the liquid storage assembly by the fixing member.

4. The atomizer as claimed in claim 3, wherein the fixing member is a lantern ring with internal threads.

5. The atomizer as claimed in claim 3, wherein a first through hole is defined on the base, the first electrode is positioned in the first through hole.

6. The atomizer as claimed in claim 5, wherein the first electrode is latched in the first through hole through a first sealing member.

7. The atomizer as claimed in claim 1, wherein:
a second through hole is defined on the atomizing head base,
the second electrode is latched in the second through hole through a second sealing member.

8. The atomizer as claimed in claim 7, wherein:
the air adjusting device consists of the outer tube and the ventilation cover,
the ventilation cover is rotatably sleeved over the outer tube,
a first ventilation portion is defined on the outer tube,
a second ventilation portion is defined on the ventilation cover,
the port size between the first ventilation portion and the second ventilation portion is adjustable by rotating the ventilation cover.

9. The atomizer as claimed in claim 8, wherein a pin bolt is positioned on the outer tube, the pin bolt is configured to limit the rotating angle of the ventilation cover.

10. The atomizer as claimed in claim 7, wherein:
the atomizer further comprises a liquid inlet tube and a liquid inlet adjusting ring,
the liquid inlet tube is sleeved over the outer tube,
the liquid inlet adjusting ring is rotatably sleeved over the circumference side of the liquid inlet tube,
a first liquid injection hole is defined on the sidewall of the liquid inlet tube,
a second liquid injection hole is defined on the liquid inlet adjusting ring,
the port size between the first liquid injection hole and the second liquid injection hole is adjustable by rotating the liquid inlet adjusting ring.

11. The atomizer as claimed in claim 1, wherein the circumference side of the atomizing tube defines at least one liquid inlet, a heating coil of the atomizing core is positioned vertically.

12. The atomizer as claimed in claim 11, wherein:
a number of the at least one liquid inlet is more than one, center axes of the liquid inlets are at a same radial section of the atomizing tube;
the number of the at least one airflow channel is more than one, the airflow channels divide the periphery of the atomizing core into several liquid inlet areas, the liquid inlet areas correspond to the liquid inlets;

each liquid inlet area of the atomizing core defines an assisting liquid inlet, each assisting liquid inlet communicates with a liquid inlet.

13. The atomizer as claimed in claim 1, wherein:
an end of the atomizing core defines at least one liquid inlet,
a heating coil of the atomizing core is positioned horizontally.

14. The atomizer as claimed in claim 13, wherein:
the atomizing core comprises an atomizing core base and a liquid absorbing element,
a concave portion is defined on the atomizing core base,
the heating coil and the liquid absorbing element are received in the concave portion,
the atomizing core base is fixed at a lower end of the atomizing tube, the second electrode is positioned on the atomizing core base.

15. An electronic cigarette, the electronic cigarette comprising an atomizer, wherein the atomizer comprising an atomizing assembly, the atomizing assembly comprising:
an atomizing head comprising an atomizing core and an atomizing tube, the atomizing tube sleeved over the atomizing core, the atomizing tube comprises an atomizing head base positioned at a lower end of the atomizing tube, an outer side of circumference of the atomizing core defining a least one airflow channel; and
a ventilation assembly fixed to an upper end of the atomizing tube, the at least one airflow channel communicating with the ventilation assembly, wherein the ventilation assembly comprises an inner tube, an outer tube and a ventilation cover, an end of the outer tube is fixed to the atomizing head base, another end of the outer tube is fixed to the ventilation cover, the outer tube is sleeved over the inner tube, an end of the inner tube is fixed to the ventilation cover, another end of the inner tube is suspended in the outer tube;
wherein, air is capable of entering the atomizing core through the ventilation assembly and the airflow channel;
the atomizer further comprises a liquid storage assembly, the liquid storage assembly defines a liquid storage cavity, an upper end of the atomizing assembly is sleeved over the liquid storage assembly, a lower end of the atomizing assembly is suspended in the liquid storage cavity, or abuts against a lower end surface of the liquid storage assembly;
the liquid storage assembly comprises a first electrode, the atomizing assembly comprises a second electrode, the first electrode is electrically connected to the second electrode;
the atomizing assembly further comprises an air adjusting device, the air adjusting device is positioned at an end of the ventilation assembly opposite to the atomizing head, the air adjusting device is configured to adjust the amount of airflow entering into the atomizer.

* * * * *